United States Patent [19]

Nugent

[11] Patent Number: 4,601,896
[45] Date of Patent: Jul. 22, 1986

[54] PHARMACEUTICAL CAPSULE COMPOSITIONS AND STRUCTURES FOR GASTRIC SENSITIVE MATERIALS

[76] Inventor: Mark Nugent, 1202 Stratford La., Algonquin, Ill. 60102

[21] Appl. No.: 591,972

[22] Filed: Mar. 21, 1984

[51] Int. Cl.[4] .......................... A61K 9/52; A61K 9/66
[52] U.S. Cl. .......................................... 424/36; 424/21; 106/124; 106/125; 106/128; 106/131; 206/530; 260/DIG. 43
[58] Field of Search ............................ 424/21, 37, 36; 106/124, 125, 128, 131; 206/530; 260/DIG. 43

[56] References Cited

U.S. PATENT DOCUMENTS

| 2,340,037 | 1/1944 | Zipper | 206/530 |
| 2,491,475 | 12/1949 | Bogin | 106/128 |
| 3,655,035 | 4/1972 | Mühlbauer | 206/530 |
| 3,655,416 | 4/1972 | Vinson et al. | 106/131 |
| 3,806,350 | 4/1974 | Kuhn et al. | 106/124 |
| 3,955,697 | 5/1976 | Valyi | 428/515 |
| 4,427,116 | 1/1984 | Brown | 424/37 |
| 4,428,927 | 1/1984 | Ebert et al. | 427/37 |

FOREIGN PATENT DOCUMENTS

| 2729007 | 1/1979 | Fed. Rep. of Germany | 206/530 |
| 2729068 | 1/1979 | Fed. Rep. of Germany | 206/530 |
| 47-37523 | 9/1972 | Japan | 424/37 |
| 85137 | 12/1935 | Sweden | 206/530 |
| 183805 | 7/1936 | Switzerland | 206/530 |

OTHER PUBLICATIONS

Chemtech Sep. 1973, pp. 552–562.

Primary Examiner—Ronald W. Griffin
Attorney, Agent, or Firm—Niblack & Niblack

[57] ABSTRACT

This invention provides oral dosage forms of therapeutic agents such as digestive enzymes which are subject to degradation and loss of activity at gastric pH. and compositions and methods for preparing same. Capsules of their components are formulated from a composition comprising a plastic homogeneous mass of gastric fluid impervious material such as cellulosic derivatives or collagenous material; from 10–65% by weight of a diluent selected from the group consisting of water, a lipid having a melting point above mammalian body temperature and a water miscible solvent; 4–60% by weight of procollagen; and 30–86% by weight of collagen or elastin. The composition is formed into finished capsules of relatively homogeneous composition comprising 10–50% by weight of procollagen and 40–96% by weight of a material selected from the group consisting of collagen and elastin, and having less than 4% by weight of fat and water-soluble protein. Prior art pH dependent enteric coat materials such as cellulose acetate phthalate may be incorporated at a level of 1.0–40%. At time of oral administration, an activator capable of dissolving the capsule wall is allowed to contact the interior surface of the capsule. In the case of cellulosic composition outer walls, cellulose or a non-enzymatic alkaline buffer is applied, and a proteolytic enzyme is employed to dissolve collagenous materials.

19 Claims, 6 Drawing Figures

PHARMACEUTICAL CAPSULE COMPOSITIONS AND STRUCTURES FOR GASTRIC SENSITIVE MATERIALS

BACKGROUND OF THE INVENTION

This invention relates to improved capsule compositions and structures of pharmaceutical compounds which are difficult to administer orally and more specifically relates to oral unitary dosage forms of therapeutic materials which are subject to degradation under gastric conditions, such as digestive enzymes, and especially pancreatic preparations of animal origin.

Digestive enzyme replacement therapy is beneficial in patients with cystic fibrosis, chronic pancreatitis, post-pancreatectomy, ductal obstructions caused by tumors of the pancreas, pancreatic insufficiency, steatorrhea of malabsorption syndrome and post-gastrectomy (Bilroth II and total) and for betagalactosidase deficiency. Many products are currently marketed for enzyme replacement therapy where pancreatic exocrine insuffiency exists. Various types of enteric-coated tablets, capsules, enzyme powders and mixtures of enzymes with anticholinergics and barbituates are included among the products which are now sold. While it is difficult to assess efficiency of the various protective means that have been employed, the large number of combinations of coatings, buffers, antiacids, $H_2$ receptor antagonists and so on, coupled with the literature's conflicting views as to their effectiveness leads to the conclusion that optimal dosage forms or regimens have not yet been developed.

Pancreatic enzymes are active under neutral or slightly alkaline conditions. In the presence of acid pH and pepsin, that is under the conditions encountered in the mammalian stomach, they are irreversibly inactivated and totally lose their biological activity. It it recognized by the art that orally administered pancreatic enzymes must be protected from degradation during passage through the stomach. While various enteric coatings have been reported in the prior art, they are hampered by several problems and have thus not been accepted without reservation because most of them are permeable to gastric fluids or they fail to disintegrate promptly upon passage into the duodenum to allow rapid mixing with the chyme so as to achieve maximum biological effect.

In the normal physiological state, the stomach contents encounter pepsin which is activated by hydrochloric acid. Both the enzymatic action of pepsin and the strong acid pH of the stomach (pH 1.2 to 1.8) destroy the activity of these enzymes. There are several problems encountered with the use of entericcoated capsules which are dependent upon pH levels for release of their activity. In a study by Regan et al, New England Journal of Medicine 297, No. 16:854-858, 1977, it was found that an enteric coated capsule released approximately 50% of the total enzyme activity in thirty minutes when incubated at pH 6 to 7. Another problem with enteric coatings of this type is that in patients with persistent steatorrhea, intragastric pH was higher during the initial forty minutes. Enzyme was probably released by the enteric coating only to be later inactivated as the pH fell below 4.

The presence of food in the gastro-intestinal tract causes the release of secretagogues that stimulate the flow of enzymes and bicarbonate by the pancreas. Enzymes of the pancreas are secreted in the form of inactivated zymogens. Upon entry into the duodenum, enterokinase converts trypsinogen which is inactive into the active form called trypsin. Trypsin catalyzes the conversion of all enzyme precursors into their active forms. The acidic mixture from the stomach is neutralized by the bicarbonate secretion of the normal pancreas. Trypsin activity is reduced to less than 10% fo its original value in fifteen minutes by incubation with pepsin at pH 1.6. Since pancreatic exocrine insufficiency often has inadequate bicarbonate secretion as a component of the disease, it is wrong to assume that reliable release of pH activated enteric coatings can work in all situations. While oral dosing is the most practical means for chronically controlling several disease states, it requires the use of gross amounts of digestive enzymes far in excess of those endogenously needed in order to compensate for gastric inactivation and to achieve delivery with effective biological activity levels into the intestinal tract.

SUMMARY OF THE INVENTION

This invention provides pharmaceutical oral unit dosage forms such as capsules, capsule components and compositions for fabricating them, which protect gastric-sensitive materials contained in the capsules from being degraded and rendered inactive as they pass through the mammalian stomach into the intestinal tract. The drug is enclosed in a capsule having a resilient outer wall which is impervious to gastric fluids. An activating material which causes dissolution or digestion of the wall is allowed to contact the interior surface of the capsule wall at time of oral administration to initiate dissolution.

Preferably the capsule is fabricated from water-insoluble native collagen and/or elastin blended with procollagen. An activating proteolytic enzyme such as collagenase is used to coat the interior surface at time of administration to initiate rapid lysing of the procollagen component compared to slower dissolution of the collagen portion. The capsule surface remains intact until the capsule has passed into the duodenum. Procollagen is rapidly dissolved by the enzymatic action while collagen and elastin are more slowly affected by it.

Dissolving of the capsule outer wall by the activator fluid results in its disruption to release the pharmaceutical in the duodenum.

BRIEF DESCRIPTION OF THE DRAWINGS

The present invention will be more readily understood from the following detailed description, taken in conjunction with the accompanying drawings in which.

DETAILED DESCRIPTION OF INVENTION

This invention relates to orally administerable medicinal dosage forms of pharmaceuticals which are gastric sensitive. By gastric sensitive is meant materials subject to inactivation upon prolonged exposure to gastric conditions such as highly acidic pH levels and pepsin. A preferred embodiment of this invention relates to digestive enzymes, particularly pancreatic material such as pancreatin. While they are necessary to normal digestion and are orally administered in the treatment of many diseases, they are rapidly and irreversibly degraded under gastric conditions.

Figure 1:
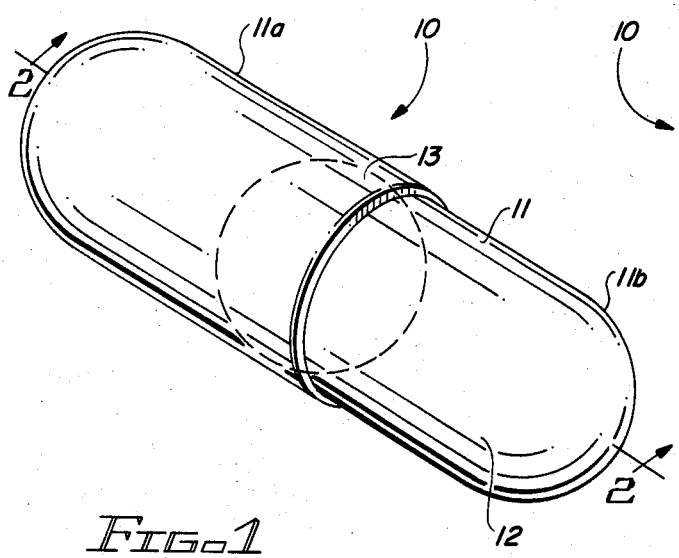
FIG. 1 is a phantom perspective view of a capsule of one embodiment of the invention having an enclosed activator-containing center sack.
Figure 2:
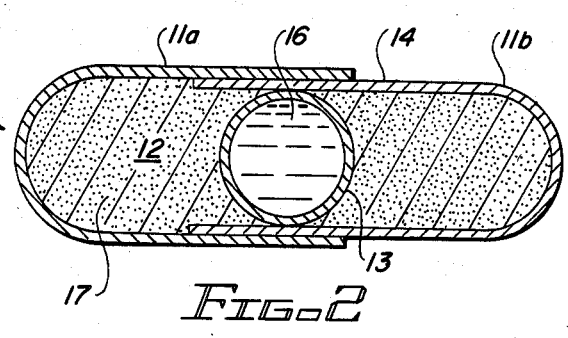
FIG. 2 is a cross-sectional view of the capsule of FIG. 1 taken along lines 2—2.
Figure 3:
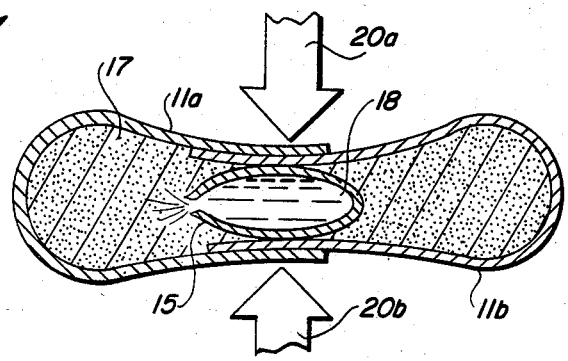
FIG. 3 is a cross-sectional view of the capsule of FIG. 1 taken along lines 2—2 and showing the capsule compressed and deformed at its midsection to transmit pressure to the interior chamber thereby rupturing the center sack.

Referring to the drawings, FIG. 1 depicts a preferred configuration of one aspect of the invention. Unit dosage form 10 is a capsule 11 formed by telescoping cape 11a and body 11b to form a sealed chamber 12. As best shown in FIG. 2, the dosage form 10 in this embodiment is a complete, self-contained, shelf-stable unit. Telescoping components cap 11a mates with body 11b to form an overlapping center seal. Thus, capsule exterior flexible wall 14 defines drug chamber 12 which contains gastric-sensitive material 17. Confined within the chamber is activator capsule or sack 13 having brittle coat 15 that forms second chamber 16 which houses activator fluid 18. The capsule is formed from a material which is impervious to gastric fluids as discussed in detail hereinbelow.

At the time of oral administration to a mammalian host, the activator fluid is released by applying pressure, i.e. squeezing, capsule 11 at centrally located points 20a and 20b to rupture sack 13, whereby the activator fluid is released into chamber 12. Following release from sack 13, the activator fluid digests the gastric-impervious capsule wall 14 to release the active medicament.

Figure 4:
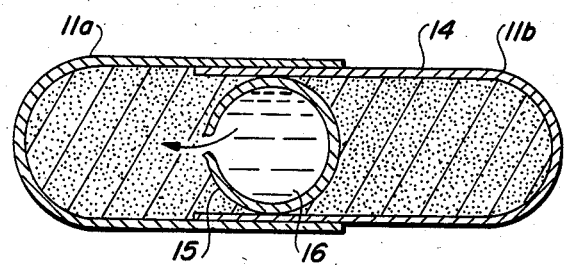
FIG. 4 is a cross-sectional view showing the capsule after release of the mid-section pressure of FIG. 3, returned to its original configuration but with ruptured center sack.

FIG. 4 depicts the externally intact capsule immediately following rupture of sack 13 to cause release of the activator fluid which then contacts the interior surface of capsule wall 14 to initiate digestion or disruption of the capsule wall. In use, the intact capsule is in the stomach of the host at this stage.

Figure 5:
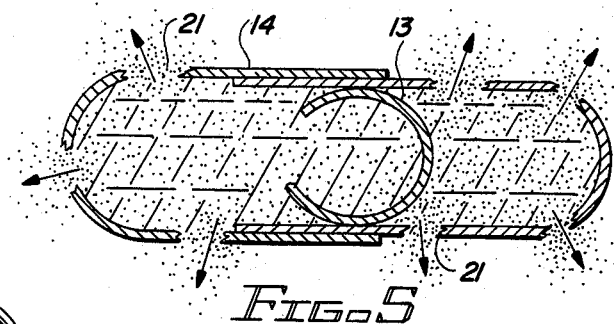
FIG. 5 is a cross-sectional time lapse view of FIG. 4 depicting disruption of the capsule outer wall to release its contents.

Referring to FIG. 5, as the capsule passes into the intestinal tract of the patient, the digestive or disruptive action of the activating fluid on the capsule wall causes rupturing of wall 14 to form multiple orifices and fissures 21 which allow release of drug from chamber 12 into the small intestine.

Figure 6:
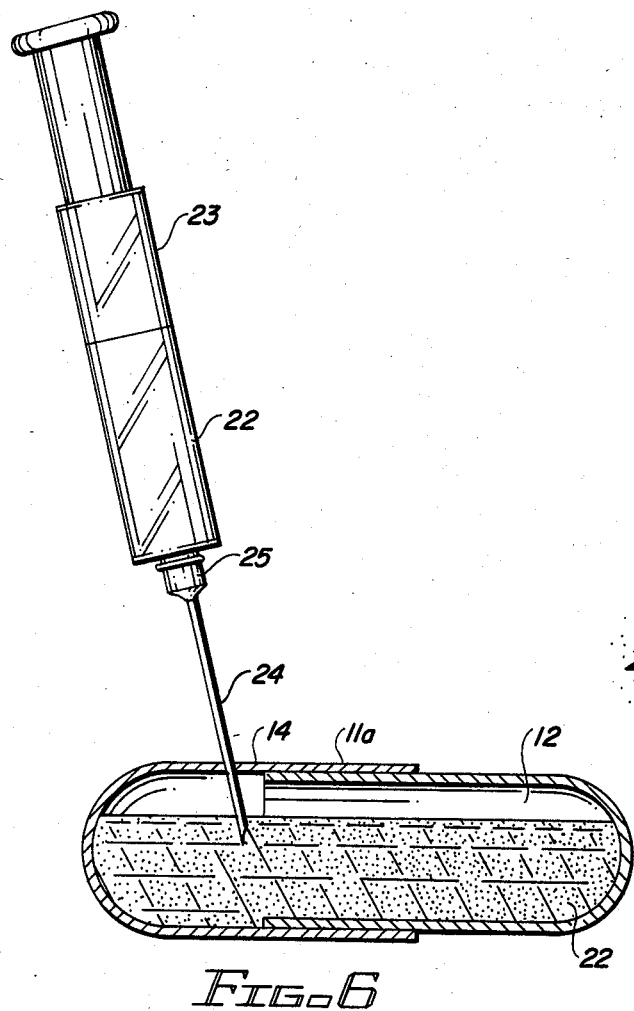
FIG. 6 is a sectional view of a second embodiment of the invention with portions cut away for clarity and understanding, depicting the filling of an empty capsule using a hypodermic needle and syringe.

FIG. 6 illustrates another embodiment of the present invention. Capsule chamber 12 remains empty until immediately before administration. Prior to administration, hypodermic needle 24 attached by luer lock 25 to syringe 23 is inserted through capsule wall 14 into chamber 12, whereupon combined drug-activator fluid 22 is injected into the chamber and the needle withdrawn. As in the embodiment illustrated in FIGS. 1–5, the capsule is formed from a material which is impervious to gastric fluids, but which is dissolved by the activator fluid. The activator fluid slowly digests the capsule walls to release the drug once the capsule has passed into the small intestine.

Collagen and/or elastin combined with procolagen are the basic components used in the preferred gastric-protective coatings of the invention.

Collagen is the fibrous, substantially water-insoluble protein found in skin, connective tissue, ligaments, and tendons of animals. It naturally exists in a solid state and cannot be made to go into water solution without hydrolysis. Collagen can be completely degraded and rendered soluble by hydrolysis to produce gelatin. When exposed to conditions which produce gelatin-type materials, it cannot be treated to regenerate it back to the native insoluble fibrous state. The term "collagen" used hereafter without modification means substantially native water-insoluble collagen. With certain treatments, a fraction of collagen can be rendered soluble in aqueous solutions from which it can be recovered in the native fibrous form. This fraction is called procollagen.

Collagen, can be prepared according to the method of Einbinder and Schubert, *J. Biol. Chem.* Vol.188: 335 (1951).

A second material which is equivalent to collagen for the purposes of this invention is elastin. Elastin which occurs with collagen in many tissues is the yellow protein exhibiting strong blue-white fluorescence found in most connective tissues of animals. It is the elastic tissue protein remaining after all other connective tissue components have been removed from the tissue. Collagen mucopolysaccharide occurs in conjunction with elastin which is the principal additional water-insoluble protein comprising the elastic fibers of most connective tissue. Elastin comprises about 30% by weight of most connective tissues, although the amount varies widely. Collagen comprises 85% of the protein content of mammal corium and fish skin. Mammalian skin consists of about 2–5% elastin; aortic tissue is 30% to 57%; and bovine ligamentum nuchae (back strap) is 78% to 80% by weight elastin.

Morphologicaly, the fibers of elastin are not of one single type as is the accepted case with collagen. In general the fibers show no ordered structure and no axial periodicity as with collagen.

While the art has developed several methods of preparing suitable elastin preparations, in general, they involve autoclaving or extraction with boiling water to remove collagen in the form of gelatin (which is neither necessary nor desirable in the present case). Cold lime water, formic acid, hot sodium hydroxide, and guanidine extraction, among others, have been successfully used to prepare various elastin preparations of suitable purity. Purity is not necessary in using the elastin-collagen material in the present invention. They are freely interchangeable and one may be substituted for the other in any percentage.

Elastin can be prepared according to the method of Partridge, Davis and Adair, *Biochem. J.* Vol 161: 11 (1955)

The collagen source of the compositions is not critical. Examples of suitable material include ground calf skin, pig skin, sheep skin, connective tissue from various mammalian species, fish swim bladder, fish skin and so on. The desirable qualities sought include low cost and ease of reducing the raw material to a plastic homogeneous and extrudable form.

In addition to the collagen-elastin, the other component of this aspect of the invention is pro-collagen. Originally the term pro-collagen was coined to identify the fraction of collagen extracted with citrate buffer from mammalian skin which could be reformed into native fibrils exhibiting banded periodicity on dialysis against water. It was so named because of the original theory, since disproven, that it was a precursor of collagen. Later the literature began to generally use the term tropocollagen to describe undegraded soluble preparations regardless of their source. The term is now used to describe the protein and not the fiber. It is therefore less ambiguous to use a self-explanatory term such as "soluble collagen". In this specification, the term "procollagen" is used to mean acid-extracted, cold acid soluble, neutral salt soluble, tropocollagen, pH relaxation extracted and like collagenous materials. Tropocollagen is formed by three alpha 1 and alpha 2 polypeptide chains. Non-helical end portions of the basic triple helix collagen structure, called telepeptides, are an integral part of tropocollagen. Proctase, as well as some other proteases, solubilize collagen which lacks portions of the telopeptide region. This telopeptide poor collagen has been referred to atelocollagen. It is included in the class of materials referred to herein as procollagen.

These materials have the property of being soluble in aqueous solutions, not being hydrolyzed and of high molecular weight. Compared to unextracted or solid state native fibrous collagen, they are more readily subject to the action of proteolytic enzymes. Native insoluble collagen is more slowly affected by the action of proteolytic enzymes. While minor, discreet chemical changes may initially occur when such enzymes act upon unextracted native collagen, these changes are without significance in the present invention.

Using various methods reported in the literature suitable classes of procollagen can be prepared for incorporation into the protective coating. Neutral salt soluble, acid-soluble, and pH relaxation extracted procollagen all yield a product that gels at 37° C. The pH relaxation extraction method is the most efficient and yields approximately 50% by weight of procollagen from the native solid state collagen available in the dermis as compared to yields of 1 to 10% for the other techniques. This method is described by Hayashi et al, *Connective Tissue Research*, Vol.1:39–46(1972). The process involves changing the pH of the extraction medium from acid to neutral and neutral to acid while maintaining the temperature at 23° to 25° C. during the extraction. References therein cite methods for preparing neutral-salt soluble and acid-extracted procollagens.

The type of procollagen chosen is dictated by convenience and cost. Purification is also not critical if the interfering extraneous matter is held to low levels. Preferably lipids and albumins are essentially eliminated. The high yield of pH relaxation extraction material makes it highly desirable. However, other types such as neutral salt extracted procollagen may be preferred, depending upon availability of raw collagenous materials. While neutral salt extracted procollagen is more difficult to purify and acid extracted contains somewhat more aggregates, they are identical for the purposes of this invention. Slight cross-linking heterogeneity and differences in the amount of lysine derived aldehyde have no effect on the enzymatic dissolving action essential to the operation of the capsule protective coat.

The basic composition of this invention suitable for fabrication into unit dosage forms such as capsules comprises a gastric fluid "inert" or impervious material which will not be disrupted by conditions in the stomach during the time interval required for the capsule to pass into the small intestine. Preferably the capsule is comprised of cellulosic material susceptible to cellulase activation or collagen materials. Most preferably, the composition is a plastic homogeneous mass of from 10% to 65% by weight of a diluent which is mixed with collagen and/or elastin native material. The water-insoluble collagen or elastin is mixed with the diluent to form a plastic material of the desired consistency for fabrication into the desired dosage forms. The diluent may consist of water or lipids having a melting point above mammalian body temperature. Water miscible solvents such as lower alkyl alcohols including isopropyl alcohol, methyl alcohol or ethyl alcohol may also be used in lower concentrations.

Suitable non-collagenous materials which may be incorporated into the capsule wall composition are materials used to enteric coat medicaments. Preferred enteric coating materials are water-insoluble cellulosic derivatives which are impervious to gastric conditions, preferably cellulose acetate phthlate.

Traditional enteric coating ingredients may be homogeneously incorporated at a level of 1% to 40% to give greater formulation latitude without adversely affecting the pH independent enzyme sensitive enteric coat action of the procollagen component. Levels higher than 40% can be used if procollagen enriched zones are inserted, as by capsule banding. While such combinations of capsule surface components have utility and may be of lower cost they are not preferred because of the more elaborate fabrication required.

A preferred embodiment comprises assembly of traditional telescoping capsule components, either a cap or body piece, with the cooperating component being the procollagen/collagen composition of the invention. Another preferred structure is composed of prior art pH dependent enteric coating material such as cellulose acetate phthalate at a level of 1% to 40% by weight blended with procollagen and collagen to form capsule components. Especially preferred is a range of from 15% to 35%. The total procollagen final level should be 10% to 50% by weight of the total composition.

More specifically, the basic composition of the present invention which is matter suitable for fabrication into housings for oral unit dosage forms of gastric-sensitive medicaments comprising: a plastic homogeneous mass of from 40 to 96 weight percent of collagen or elastin having substantially all naturally occurring lipids and water-soluble protein removed therefrom; from about 10 to 50% weight percent of procollagen; and sufficient diluent to render said mass pliable for fabrication.

The nature of the diluent is not critical as the mechanical consistency and formability of the collagenous mass is of primary concern. Procollagen at a level of about 10% to 50% by weight is incorporated into the blend. Purity of the basic collagenous or elastin material is not critical although limitations should be observed as to the amount of fat and extraneous water soluble proteins such as albumin. These extraneous materials should not exceed 4% by weight of the final blend on a dry weight basis.

In this aspect, the critical point to the operation of the invention is utilization of the differential action of proteolytic enzymes on lysing of procollagen compared to the relatively less reactive nature of collagen/elastin materials. Procollagen is highly susceptible to dissolution by these enzymes while native collagen and elastin are somewhat resistant and are more slowly dissolved thereby. Thus, the basic process involves the preparation of a sheet, tube or shell of active collagen and/or elastin having low levels of interfering extraneous matter, susceptible to being leached or dissolved during passage through the stomach; addition of a film-disrupting level of procollagen which when dissolved or lysed by proteolytic enzyme allowed to come into contact with it at time of oral administration, will cause disruption of the entire protective film shielding the drug encapsulated within it. The simplest preferred embodiment is formation of a capsule consisting of a continuous gastric fluid-impervious layer of collagen/elastin material combined with procollagen. Inside the surface layer and contacting it is an activating layer of proteolytic enzyme capable of lysing the procollagen component. One expedient method of achieving this structure is to prepare, from the basic plastic mass, empty capsules containing no drug. These blanks are then charged with a mixture of active drug and proteolytic enzyme by injection just prior to oral administration. The enzyme initiates disruption of the coating interior while the capsule passes through the stomach. Upon reaching the pylorus, the protective wall is ruptured and its contents are exposed to the alkaline conditions of the duodenum.

Appropriate buffers may be added to the basic drug formulations. This is often advantageous because of the insufficiency of natural pancreatic bicarbonate secreted in some digestive disease conditions.

While it is sometimes desirable to employ a very high percentage of collagenous material in the protective coat, it is often advantageous to incorporate substantial amounts of gastric resistant conventional coating materials such as those used in typical enteric formulations. These may be used in amounts up to about 40% by weight although lesser levels are preferred. The procollagen total level of the blend should be maintained in the 10% to 50% range. Usually these will be homogeneously blended with the collagen-derived ingredients although capsule components or outer coating segments of the dosage form such as rupture-bands or grids composed essentially of procollagen/collagen or elastin can be spaced in the capsule surface. A simple example of such structures is striping as by fixing a collagenous blend center band to a capsule by cementing it to conventional enteric capsule ends. Another expedient is to provide a capsule cap component of collagenous blend and a conventional enteric body portion, or vice versa.

Substituting other enteric coatings has the advantage of allowing the formulator greater latitude in reducing costs by using cheaper ingredients and adding elegance characteristics such as high gloss and other appearance factors to the final coat surface.

The internal disrupting activator which is independent of host intestinal pH values remains effective while allowing use of a broad range of ingredients.

A suitable conventional enteric coat is prepared by dissolving one part by weight of cellulose acetate phthalate in two to two and one-half parts of 2.0% aqueous ammonium hydroxide, and them adding 1 part of hydroxypropyl methylcellulose. The mixture is heated to complete solution; and the resulting solution again heated under reduced pressure to remove excess ammonia. Cap or body mold pins are submerged into this dipping solution, slowly removed to solidify and air dried to provide enteric hard shell capsule components.

A shelf stable complete dosage form is provided in one preferred embodiment. The active material is combined with proteolytic enzyme and encapsulated within a rigid film coat, many examples of which are known to the prior art, e.g. beeswax, paraffin, cellusose acetate phthalate, hydrogels having short and non-elastic crosslinks which are brittle in the dry state, unplasticized gelatin of low Bloom strength, and the like. This coating may be referred to as a crack coating which is easily broken by squeezing the capsule exterior. The protective procollagen coating then covers the crack coating. At time of administration pressure is applied to the exterior to fracture the crack coat, which causes the enzyme to contact the outer coat and initate dissolution.

An especially preferred embodiment includes the use of an elastic outer coating. One convenient technique for achieving this structure is to include a soft elastic outer layer that will facilitate application of surface pressure to deform and rupture the rigid inner layer. To achieve this, it is desirable to incorporate plasticizer into the collagen protective coat to insure that surface manipulation does not cause fissures to develop in the coating prior to internal digestion by the activating fluid. The outer squeeze coat is formed by applying a soft elastic capsule exterior in which gelatin is plasticized by adding a polyol such as glycerin or sorbitol. Methods of making such gelatin coatings are well known to the capsule art.

One method of applying such a coat is by means of the Accogel capsule machine which uses rotary dies capable of enclosing capsules, tablets, and slugs in a gelatin film.

The finished capsule of this embodiment thus consists of three or four layers: the exterior elastic film which is used merely to facilitate deformation and application of rupturing pressure to the interior of the capsule, the protective procollagen layer below the surface layer and the proteolytic enzyme plus drug blend within the capsule center. The fourth layer may alternatively encase the proteolytic enzyme separated from the drug. In this configuration the drug is placed in the center of the capsule and surrounded by crack coatings or rupturable membranes. The proteolytic enzyme is deposited on this coating and covered by the outer brittle coating, preferably beeswax. While this results in a more complex and expensive structure, it has the advantage of segregating the activating enzyme which increases shelf life of the product in some cases by avoiding changes in the drug that may be hastened by blending it with the enzyme. Because of the microbially nutritive nature of the protective coat, it is desirable to incorporate preservatives into the surface. This is also true of the top elastic coat. Preservatives, preferably the parabens, parahydroxybenzoic acid lower alkyl esters, at a concentration of up to about 0.2% are advantageously added to prevent growth of fungi and other micro-organisms.

Plasticizers such as high molecular weight polyethylene glycols, preferably having a molecular weight of about 8,000 may be incorporated into the film surface. Low levels of these materials should be used unless they are restricted to the coating surface. While glycols have desirable softening properties, they are themselves water-soluble and may thus lower integrity of the protective film under gastric conditions if used at higher concentrations. Therefore, very low levels should be incorporated or their presence confined to the upper or exterior surface portions of the film.

There are various optional methods of stabilizing the outer shell of the capsule to the gastric environment. Tanning and reducing agents can be used to provide chemical modification for improved resistance to gastric secretions. While such treatment is ordinarily not preferred because of the problem of unduly increasing the resistance to enzyme digestion, toughening of the surface can be used to provide increased stabilization of the exterior shell from gastric conditions.

Activating enzymes which are brought into contact with the procollagen coat at time of administration can be selected from a broad class of proteolytic enzymes. The primary considerations regarding the choice of enzyme is the pharmaceutical acceptability and the ability to lyse procollagen at a predictable rate. Examples of enzymes which may be employed are the following: chymotrypsin, alpha-chymotrypsin, bromelain, collagenase, elastase, fibrinolysin, desoxyribonuclease, trypsin, papain, subtilins, amylase, carboxypeptidase A and B, beta-galactosidase, enzymes of the intestinal brush border, ficin, other therapeutic enzymes of plant or bacterial origin and the like.

The concentration of enzyme is dependent on two factors: the length of time required to dissolve the outer coat and cause its rupture which is a function of the enzyme activity; and the thickness of the protective coat. As a general rule, the more concentrated the enzyme, the more desirable the formulation. Concentration is desirable because the shelf life of many enzymes is shortened in suspensions and solutions or when mixed with other materials. To extend the storage life of the completely loaded capsules, it is desirable to isolate the activating enzymes in a dry layer between the drug and the collagenous outer coat. The simple expedient of mixing the enzyme with drug at time of administration obviates the problem of shelf life encountered when the ingredients are pre-blended. Even then it is advantageous to keep moisture as low as possible and rely upon the drug moisture level to initiate proteolytic action.

An alternative is to provide a fluid reservoir or layer in the capsule interior. Illustrative of this expedient, drug and activator are blended and frozen in pellet form. The frozen pellet is dipped into molten crack coat dip, preferably beeswax. After solidifying the coated frozen pellet is dipped in liquid solution compatible with the activator fluid. The dip solution may include saline solution, lactated Ringer's solution, trishydroxyaminomethane buffer or sodium bicarbonate solution. Heat transmitted out of the moisture layer freezes and solidifies it. Thereafter, the protective enteric coat is applied.

Beeswax is the preferred crack coat ingredient because it is pharmaceutically acceptable and hardens to form a slightly elastic film that is of sufficient brittleness to predictably rupture. Other edible waxes such as carnauba or blends of paraffin having similar hardness properties with modest pliability are also very useful.

Rate of film disruption can be varied by altering concentrations of the activating fluid. Collagenase, for example, suspended in lactated Ringer's solution buffered to pH 8 with bicarbonate may be used by injecting the concentrated mixture into the center of a capsule having a wall thickness of 2 mils to achieve its rupture within one hour. Using serial dilutions of collagenase, capsule rupture can be adjusted to occur at varied times within a 24 hour period. Timing can be readily calibrated in vitro using the particular activating enzyme system chosen.

The following examples further illustrate the present invention.

EXAMPLE 1

Preparation of Insoluble Collagen

Cattle achilles tendon is cleaned of all non-collagenous tissue, cut into small pieces and extracted for six days of 0° C. in 3% Na HPO to remove soluble proteins. The solution is changed daily during the extraction. Removal of mucopolysaccharides is accomplished by extraction for six days at 0° C. in 25% potassium chloride solution. The tendon residue consisting of purified collagen is then thoroughly washed with water, dehydrated with absolute alcohol and air dried.

EXAMPLE 2

Extraction of Neutral Salt Soluble Procollagen

Corium from week old calf skin is cut into strips and coarsely ground in a meat grinder under refrigerated conditions to avoid excessive heating. All processing steps are performed at 0° to 5° C. Aliquots of wet tissue are extracted for 18 hours on a shaking machine with 50 to 100 ml of salt solution comprised of equal portions of $Na_2HPO_4$ and $NaH_2PO_4$ at pH 7.0. Two extractions of the tissue aliquot are carried out. The extracts are separated from the tissue by centrifugation at 80,000 x g for one hour and then passed through sintered glass filters. The filtrates are dialyzed against repeated changes of cold distilled water. The precipitates formed are separated by centrifugation, washed in water in the centrifuge and lyophilized.

EXAMPLE 3

Preparation of Acid-soluble Procollagen

Acid-soluble procollagen is prepared from the corium of young calf skin. After removing the epidermis and subcutaneous tissue from the corium, it is ground in a meat grinder, keeping the blades cold by ice addition. Ground corium is pre-extracted with cold solutions of 0.5 M sodium acetate four times. This residue is washed with cold distilled water three times and then extracted with 0.075 M citrate buffer, pH 3.7, at 0° to 5° C. The citrate extract of calf skin is clarified by centrifugation and dialyzed against 0.02 M disodium hydrogen phosphate solution. The resulting fibrils are harvested, washed with cold, distilled water, resuspended in water and lyophilized.

EXAMPLE 4

Capsule Preparation

Capsules were formed using beef intestine casing as a form. One end of the casing was tied and the open end placed over the top of a syringe. The casing was inflated and the open end tied off. The inflated casing has a diameter of approximately 1.0 cm. The casing was suspended within a round plastic mold with approximately 0.5 cm of space between the outer wall of the casing and the inner wall of the plastic mold. Approximately 100 mg of acid-soluble procollagen was added to 15 ml of 0.1 M acetate buffer, pH 3.8 at 0° C., and left overnight at that temperature. After the procollagen was in solution, sodium hydrogen carbonate was added until the solution attained pH 6–8. Collagen (100 mg) was added to this solution and mixed thoroughly. A syringe was charged with this highly viscous solution and the solution was injected through a hole in one end of the mold. The hole was closed after filling the mold and the capsule placed in a 37° C. water bath for 2 hours. Gelation occured rapidly and the collagen capsule was removed from the mold following gelation. The capsule was allowed to lose water on Watman filter paper until it attained approximately 20% of its original thickness. The capsule core was suspended three additional times within the plastic mold and the above steps repeated until the capsule wall was 3–4 mm in diameter. The final product was a pliable, fluctuant capsule which retains its original shape upon digital compression.

Approximately 10 mg of collagenase from Clostridium Histolyticum having 420 units of activity/mg of solids is dissolved in 1.0 ml of lactated Ringer's solution. This solution was injected into the center of the capsule with a U-100 insulin syringe. The capsule wall ruptured within 50–60 minutes leaving a 3–5 mm hole in the capsule.

EXAMPLE 5

Encapsulation of buffer solution required to activate the proteolytic enzyme is accomplished as follows. Beeswax is gently melted and maintained in a hot water bath at a temperature below 85 degrees C. Isotonic saline solution, pH 7.0, is frozen into solid pellets weighing approximately 150 mg. The frozen pellets are rapidly dipped into the molten wax to apply a thin film of solidified wax. Dry enzyme and drug is applied to the waxed pellet and the complete dosage unit is formed by application of the final enteric coat.

EXAMPLE 6

Liquid buffer solution crack pellets are formed in the following manner. A curved bottom glass tube is lubricated with liquid vegetable oil. Molten beeswax is poured on the tube sides to form a hollow cap. Upon solidifying the cap is filled with isotonic saline solution and sealed by layering molten wax on top of the solution to form a seal upon cooling. Enzyme and drug are added to the outside of the wax capsule and an outer enteric coat digestible by the enzyme is applied. At time of use the outer coat is compressed digitally to rupture the wax capsule within. Gentle mixing of the ingredients is accomplished by shaking to insure proper activation of the enzyme/buffer system.

A marked advantage of this invention over prior art enteric coated compressed tablets is the gentle handling of the enzyme materials. High compression loads used to mill such materials and form tablets or beads cause partial inactivation of the enzymes. The present invention minimizes that problem and also avoids the necessity of using excipients or fillers which decrease the overall unit activity of the drug on a per milligram basis.

The above examples and detailed descriptions are given only for ease of understanding. No unnecessary limitations should be suggested therefrom, as modifications will be obvious to those skilled in the art.

The invention claimed is:

1. A pharmaceutical capsule blank adapted for oral administration of gastric-sensitive therapeutic agents, said capsule blank fabricated from a composition comprising a substantially homogeneous and gastric-fluid impervious composition comprising from about 10 to 50 percent by weight of procollagen, from about 40 to 96 percent by weight of at least one material selected from the group consisting of collagen and elastin, and less than 4 weight percent fat and albumin derived from said collagen or elastin source.

2. The capsule blank of claim 1, said blank including a chamber for containing a therapeutically effective amount of a gastric-sensitive medicament and a proteolytic enzyme capable of lysing said procollagen.

3. The capsule blank of claim 1, said blank including a first interior chamber for containing a therapeutically effective amount of a gastric-sensitive medicament and a second chamber adapted to releasably contain a material capable of dissolving the walls of said capsule blank when said material is released from said second chamber.

4. The capsule blank of claim 1 wherein said procollagen is present in an amount of from 10 to 20 weight percent.

5. A pharmaceutical capsule adapted for oral administration of a gastric-sensitive therapeutic agent, said capsule comprising an outer housing, said housing containing a first chamber, said first chamber filled with a therapeutically effective amount of said therapeutic agent; a second chamber, said second chamber containing an activator material capable of dissolving said capsule; said second chamber being contiguous to said housing, said housing comprising 10 to 50 percent by weight of procollagen, 40–96 weight percent of a material selected from the group consisting of collagen and elastin, and containing less than 4 weight percent fat or protein derived from said collagen or elastin.

6. The capsule of claim 5 wherein said housing is deformable whereby external deforming pressure may be applied to said capsule surface to cause rupturing of said second chamber, thereby allowing escape of said activator from said second chamber and contact of said activator with said housing.

7. The capsule of claim 5 wherein said activator material is a proteolytic enzyme capable of lysing said procollagen.

8. The capsule of claim 5 wherein said housing additionally comprises from 15 to 35 weight percent of cellulose acetate phthalate.

9. A composition of matter suitable for fabrication into housings for oral unit dosage forms of gastric-sensitive medicaments comprising: a plastic homogeneous mass of from 40 to 96 weight percent of collagen or elastin having substantially all naturally occurring lipids and water-soluble protein removed therefrom; from about 10–50 weight percent of procollagen; and sufficient diluent to render said mass pliable for fabrication.

10. The composition of claim 9 additionally comprising from 1.0% to 40% by weight of pH dependant non-collagenous enteric pharmaceutically acceptable coat composition, provided that the procollagen level is 10% to 50% by weight of the total composition.

11. The composition of claim 9 additionally comprising from 15% to 35% by weight of cellulose acetate phthalate, provided the procollagen content is 10% to 50% of the total weight.

12. A pharmaceutical oral unit dosage form for administering gastric-sensitive materials to a mammalian host comprising: a capsule having a resilient outer wall which is impervious to gastric fluids, said outer wall defining a first chamber adapted to house a therapeutically effective amount of a gastric sensitive medicament; said unit dosage form further including pharmaceutically acceptable activator fluid contained within said capsule, said fluid causing digestion of said capsule wall on a timed basis so as to release said gastric-sensitive medicament into the lower intestinal tract.

13. The unit dosage form of claim 12 wherein said chamber is filled with said gastric sensitive medicament and said pharmaceutically acceptable activator fluid immediately prior to administration of said capsule.

14. The unit dosage form of claim 12 wherein said capsule further comprises a second chamber, said second chamber housing said pharmaceutically acceptable activator fluid which is released into said first chamber when said second chamber is ruptured.

15. The unit dosage form of claim 14 wherein said second chamber is defined by a brittle wall capable of rupturing when external deforming pressure is applied to said resilient capsule wall.

16. A pharmaceutically acceptable oral unit dosage composition which is substantially homogeneous and gastric-fluid impervious comprising from about 10% to 50% procollagen by weight and at least 40% by weight of at least one material selected from the group consisting of collagen and elastin, substantially free of native fat and water-soluble protein.

17. A method of administering a therapeutically effective amount of a gastric-sensitive medicament to a patient in need of said treatment comprising orally administering said medicament to said patient in a housing which is impervious to gastric fluid, said unit dosage form including an activator which dissolves said housing at a pre-determined time so as to predictably release said medicament into the intestinal tract of said patient.

18. The method of claim 17 wherein said medicament and said pharmaceutically acceptable activator are introduced into said housing immediately before administration.

19. The method of claim 17 wherein said medicament and said pharmaceutically acceptable activator are present in a finished unit dosage form, said unit dosage form comprising a housing which includes a first chamber and a second chamber, said first chamber containing said medicament and said second chamber containing said activator, said activator being released when pressure is applied to said unit dosage form so as to rupture a wall of said second chamber thereby releasing activator whereby said activator contacts and dissolves said housing, releasing medicament into said patient's intestinal tract.

* * * * *